(12) United States Patent
Xia (10) Patent No.: US 7,888,027 B2
(45) Date of Patent: Feb. 15, 2011

(54) MEASURING ANALYTES USING COMPETITIVE INTERFERENCE AND RECUPERATION OF ENZYME ACTIVITY

(75) Inventor: Dongyuan Xia, Hayward, CA (US)

(73) Assignee: BioChain Institute, Inc., Hayward, CA (US)

( * ) Notice: Subject to any disclaimer, the term of this patent is extended or adjusted under 35 U.S.C. 154(b) by 102 days.

(21) Appl. No.: 12/126,827

(22) Filed: May 23, 2008

(65) Prior Publication Data

US 2009/0017459 A1 Jan. 15, 2009

Related U.S. Application Data

(63) Continuation-in-part of application No. 12/004,281, filed on Dec. 20, 2007.

(60) Provisional application No. 60/879,988, filed on Jan. 11, 2007.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 4,921,788 A | 5/1990 | Deutsch et al. | |
| 5,656,731 A | 8/1997 | Urdea et al. | |
| 5,665,539 A | 9/1997 | Sano et al. | |
| 5,849,478 A * | 12/1998 | Cashman | 435/6 |

OTHER PUBLICATIONS

Yolov et al. (Nucleic Acids Res. Jul. 11, 1990;18(13):3983-6).*
Ahn, S.J., et al., PicoGreen Quantitation of DNA: Effective Evaluation of Samples Pre- or Post-PCR. Nucl. Acids Res. 1996, 24(13), 2623-2625.
Chevalier, J., et al., Biotin and Digoxigenin as Labels for Light and Electron Microscopy in Situ Hybridization Probes: Where do We Stand? The Journal of Histochemistry and Cytochemistry, 1997, 45(4), 481-491.
Didenko, V., et al., DNA Probes Using Flurorescence Resonance Energy Transfer (FRET): Designs and Applications, BioTechniques, Nov. 2001, 31, 1106-1121.
Goldsby, R.A., et al., (2003) Enzyme-Linked Immunosorbent Assay, in Immunology, 5th ed. (1926) 148-150, Freeman, New York.
Hubscher, U., et al., Eukaryotic DNA Polymerases, Annual Review of Biochemistry, Jul. 2002, 71, 133-163.
Kaboev, O., et al. Improved RecA-assisted Fluorescence Assay for DNA Strand Exchange Reaction, BioTechniques, Jun. 2006, 40(6), 736-738.
Little, J.W., Lambda Exonuclease, Gene Amplif. Anal. 1981, 2, 135-145.
Porstmann, T., et al, Enzyme Immunoassay Techniques, An Overview, J Immunol Methods, Jun. 1992, 150(1-2), 5-21.
Ronaghi, M., et al., A Sequencing Method Based on Real-time Pyrophosphate, Science, Jul. 17, 1998, 281,363-365.
Tolun, G., et al., A Real-time DNase Assay (ReDA) Based on PicoGreene Fluorescence, Nucleic Acids Research, 2003, 31(18),e111.
Wittwer, C.T., et al., Continuous Florescence Monitoring of Rapid Cycle DNA Amplification, BioTechniques, Jan. 1997, 22, 130-138.
Wittwer, C.T., et al., The LightCycler™: A microvolume multisample fluorimeter with rapid temperature control, BioTechniques, Jan. 1997, 22, 176-181.
Yalow, R.S., Immunoassay of Endogenous Plasma Insulin in Man, J Clin Invest Jul. 1960, 39(7), 1157-75.
Yang, X., et al., Homogeneous Enzyme Immunoassay Modified for Application to Luminescence-Based Biosensors, Anal, Biochem., Jan. 2005, 336(1), 102-107.
Neimeyer, C.M., et al., Combination of DNA-Directed Immobilization and Immuno-PCR: Very Sensitive Antigen Detection by Means of Self-Assembled DNA-Protein Conjugates, Nucleic Acids Research, 2003, 31(16), e90.
Neimeyer, C.M., et al., Immuno-PCR: High Sensitivity Detection of Proteins by Nucleic Acid Amplification, Trends Biotechnolo, Apr. 2005, 23(4), 208-216.

* cited by examiner

*Primary Examiner*—Christopher M. Babic
(74) *Attorney, Agent, or Firm*—Syndicated Law; Brian S. Boyer (57) ABSTRACT

The present teaching generally discloses a method of measuring the concentration of an analyte in a solution. The method includes selecting a binding compound; selecting an analog to an analyte and conjugating the analog to a polynucleotide substrate to construct a reagent for measuring the amount of the analyte in an assay solution using a desired polynucleotide reaction that comprises a polymerization reaction, a cleavage reaction, or a recombination reaction. The binding of the reagent to the binding compound in the assay solution competes with the binding of the analyte to the binding compound in the assay solution. The method also includes selecting a desired enzyme for catalyzing the desired polynucleotide reaction. Reagents and kits are also provided.

23 Claims, 8 Drawing Sheets

MEASURING ANALYTES USING COMPETITIVE INTERFERENCE AND RECUPERATION OF ENZYME ACTIVITY

CROSS-REFERENCE TO RELATED APPLICATIONS

This application is a continuation-in-part of U.S. application Ser. No. 12/004,281, filed Dec. 20, 2007, which claims the benefit of U.S. Provisional Application No. 60/879,988, filed Jan. 11, 2007, both of which are hereby incorporated by reference in their entirety.

INCORPORATION OF MATERIAL SUBMITTED ON COMPACT DISC

The instant application contains a sequence listing which has been submitted as paper copy and a computer readable form (CRF) in U.S. application Ser. No. 12/004,281, filed Dec. 20, 2007, wherein the CRF is identical to the paper copy, and both the paper copy and the CRF are hereby incorporated by reference in their entirety.

BACKGROUND OF THE INVENTION

1. Field of the Invention

The present teaching is directed to methods of measuring an analyte in solution with a polynucleotide and a binding molecule, wherein the methods use competitive interference and recuperation of enzyme activity.

2. Description of the State-of-the-Art

The quantitative and qualitative measurement of analytes in a sample are used on a regular basis in chemistry and medicine. Immunoassays, for example, are typically binding assays used in detecting analytes that can include, for example, viral and bacterial antigens, immunoglobulins, hormones, cells, pharmaceuticals, toxins, and controlled drug substances. Since these techniques often lack in a desired amount of sensitivity and precision, amplification systems have been developed.

Many different immunoassays for qualitative and quantitative detections of analytes in a sample have been developed, such as enzyme-linked immunosorbent assay (ELISA), radioimmunoassay (RIA), and enzyme immunoassay (EIA). Immunoassays, for example, can be configured as heterogenous or homogenous assays, where a heterogenous assay is a two phase assay having solid and liquid phases, and a homogenous assay operates as a single phase. Heterogenous phase assays, such as ELISA, are commonly used, but they unfortunately require more steps than homogenous assays. Moreover, in addition to requiring the additional washing steps, the heterogeneous assays suffer in that they can never truly be automated. There are existing homogeneous phase assays, such as Enzyme Fragment Complementation (EFC), for example. EFC is a homogeneous assay based on antibody-antigen binding but, unfortunately, it has a poor sensitivity and resolution, in that it typically works for small antigens only, and only in assays having a high background activity.

A problem is that the currently available assays all require a skilled technician, only a few of the techniques have been successfully adapted for measurements of select analytes, and none of the techniques are homogenous and sensitive to a variety of analytes and under a variety of assay conditions. Accordingly, one of skill will appreciate a homogenous assay that is easy to use, takes less time than heterogeneous assays, has a high sensitivity and precision, and is capable of automation.

SUMMARY OF THE INVENTION

The teachings provided herein are generally directed to methods of measuring an analyte in solution with a polynucleotide and a binding molecule, wherein the methods use competitive interference and recuperation of enzyme activity. The teachings are also directed to reagents and kits for use in practicing the method.

In some embodiments, the teachings are directed to a method of measuring the concentration of an analyte in a solution. The method includes selecting a binding compound; selecting an analog to an analyte and conjugating the analog to a polynucleotide substrate to construct a reagent for measuring the amount of the analyte in an assay solution using a desired polynucleotide reaction. The binding of the reagent to the binding compound in the assay solution competes with the binding of the analyte to the binding compound in the assay solution. The method also includes selecting a desired enzyme for catalyzing the desired polynucleotide reaction.

After the components have been selected and constructed, the relative amounts of the components can be selected for use in the method. As such, the method further includes determining a desired ratio of the binding compound to the reagent for a given concentration of the analyte in the assay solution and a preselected amount of the desired enzyme.

An assay solution is then created and contains an amount of the binding compound and the analyte in the amount to be measured. An amount of the reagent is then added to the assay solution, wherein the amount of the reagent and the amount of the binding compound provides the desired ratio of the binding compound to the reagent. The preselected amount of the desired enzyme is then added to the assay solution to catalyze the desired polynucleotide reaction. The activity of the desired enzyme is then measured during the desired polynucleotide reaction to determine the amount of the analyte in the assay solution. Examples of methods for measuring enzyme activity include, but are not limited to, fluorescence and absorbance measurements known to those of skill.

In some embodiments, the binding compound comprises a ligand binding molecule, an antibody, or a cellular receptor. In some embodiments, the analog comprises a structure of the analyte or is a compound having the molecular structure of the analyte. In some embodiments, the polynucleotide substrate comprises a polynucleotide primer, a polynucleotide template, or a combination thereof. In some embodiments, the polynucleotide substrate is a double-stranded DNA or a single-stranded DNA.

In some embodiments, the desired polynucleotide reaction comprises a nucleotide polymerization reaction, a nucleotide cleavage reaction, or a combination of a nucleotide polymerization reaction and a nucleotide cleavage reaction. In some embodiments, the desired polynucleotide reaction comprises a nucleotide recombination reaction.

In some embodiments, the teachings are directed to a reagent for a competitive binding assay. The reagent can comprise a polynucleotide substrate conjugated to an analog, and the analog can be selected to (i) bind to a preselected binding compound in an assay solution; and (ii) compete with a binding of an analyte to the preselected binding compound in the assay solution. The polynucleotide substrate can be selected to participate in a desired polynucleotide reaction that is inhibited or quenched by the binding of the binding compound to the analog in the assay solution.

In some embodiments, the teachings are directed to a competitive assay binding kit for measuring the amount of an analyte in an assay solution. The kit comprises the reagent described above, as well as a binding compound for use in a competitive binding assay, wherein the binding of the reagent to the binding compound in an assay solution competes with the binding of an analyte to the binding compound in the assay solution. The kit also includes an enzyme for catalyzing a desired polynucleotide reaction, wherein the activity of the enzyme is measured to determine the amount of the analyte in the assay solution.

DETAILED DESCRIPTION OF THE INVENTION

The teachings provided herein are generally directed to methods of measuring an analyte in solution with a polynucleotide and a binding molecule, wherein the methods use competitive interference and recuperation of enzyme activity. Homogeneous assays are included in the teachings provided herein. The teachings are also directed to reagents and kits for use in practicing the methods.

In each of the methods taught herein, the extent of a polynucleotide reaction is used as measure of the amount of an analyte in solution. In some embodiments, the polynucleotide reactions can be polymerization reactions using a polymerase, cleavage reactions using an exonuclease, a cycling of polymerization and cleavage reactions using a cycling of a polymerase and an exonuclease, or a recombination reaction.

Figure 1:
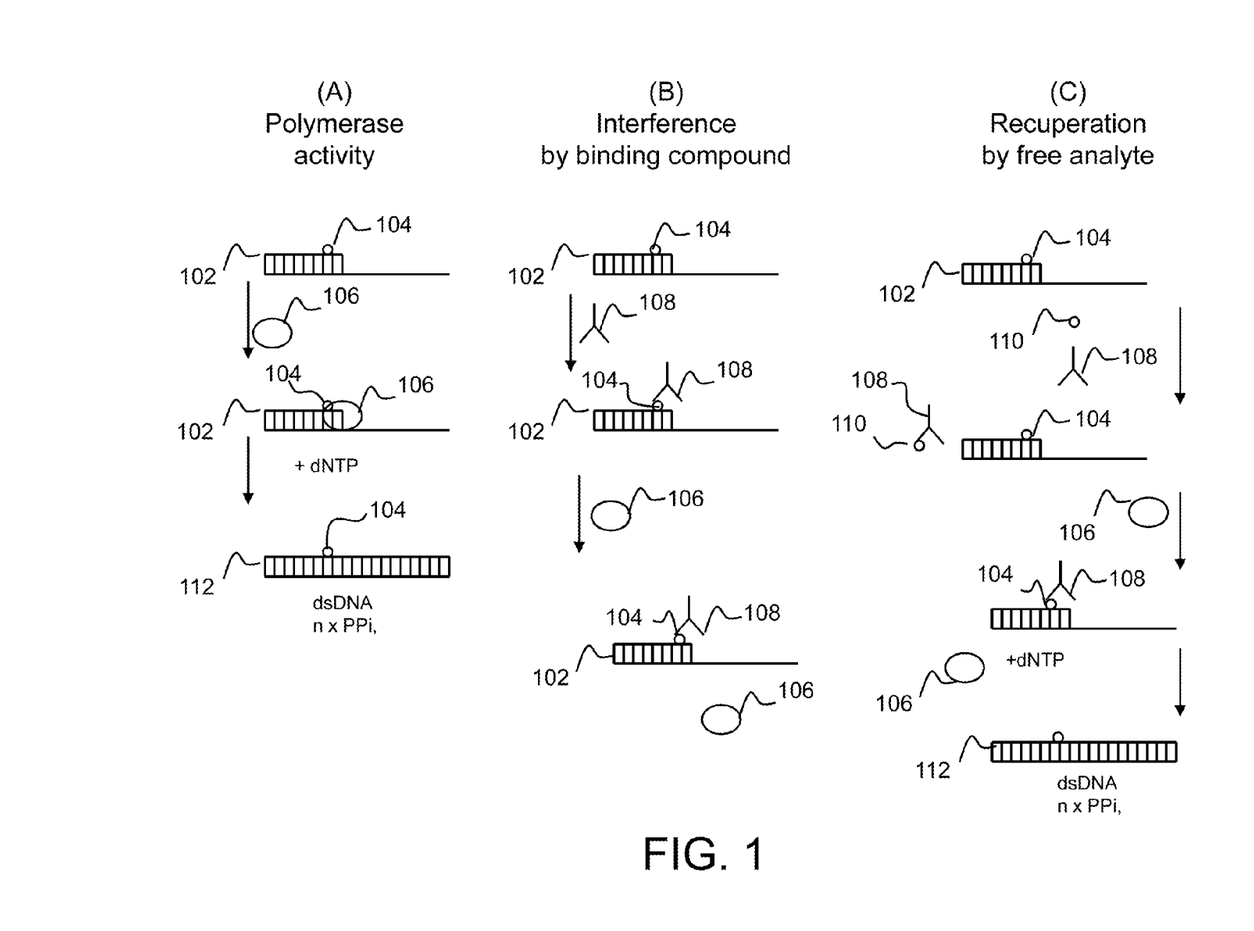
FIGS. 1A through 1C illustrate the principles of interference and recuperation of polymerase activity, according to some embodiments.

FIGS. 1A through 1C illustrate the principles of interference and recuperation of polymerase activity, according to some embodiments. Without intending to be bound by any theory or mechanism of action, the interference and recuperation of polymerase activity is believed to occur as follows. FIG. 1A illustrates a polymerization reaction catalyzed by polymerase 106, wherein the polynucleotide substrate 102 is conjugated to an analog 104. The combination of the polynucleotide substrate 102 and the analog 104 can be a reagent in some embodiments. The analog 104 is selected to bind with a preselected binding compound 108 and interfere with the polymerization reaction. In FIG. 1A, a polymerase 106 is used in the polymerization reaction to create a double stranded polynucleotide 112. In FIG. 1B, the binding compound 108 binds to the analog 104 and interferes with the polymerization reaction, such that the polymerization reaction is inhibited or quenched by the addition of the binding compound 108. In FIG. 1C, an analyte 110 that can also bind with the binding compound 108 competes with the analog 104 for binding to the binding compound 108. The competition for binding ties up a portion of the available binding compound 108 and, accordingly, results in a recuperation of the some of the polymerization reaction and production of the double-stranded polynucleotide 112. The amount of analyte present determines the amount of recuperation and, thus, the amount of recuperation provides a measure of the amount of analyte present.

Figure 2:
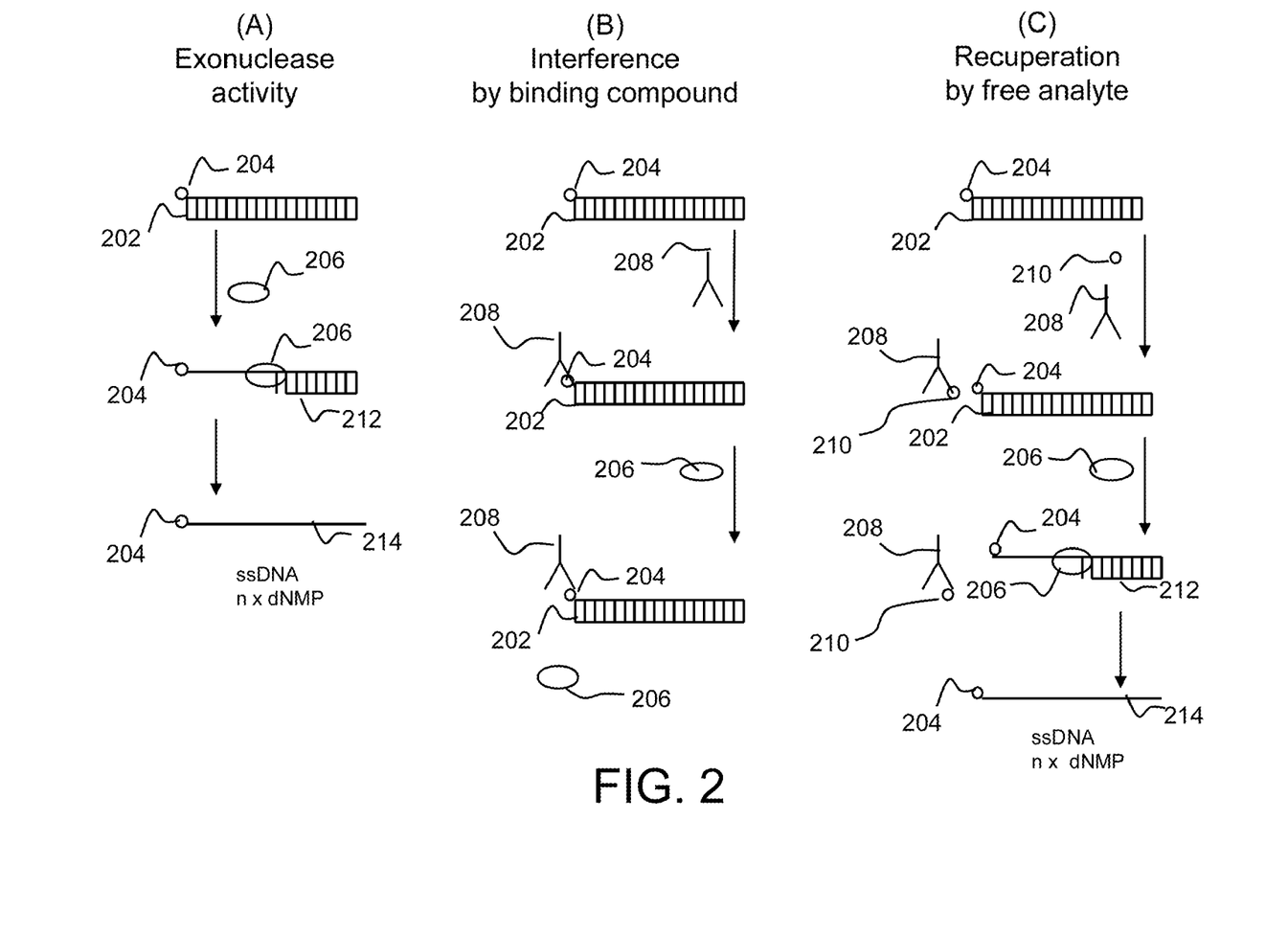
FIGS. 2A through 2C illustrate the principles of interference and recuperation of exonuclease activity, according to some embodiments.

FIGS. 2A through 2C illustrate the principles of interference and recuperation of exonuclease activity, according to some embodiments. Without intending to be bound by any theory or mechanism of action, the interference and recuperation of exonuclease activity is believed to occur as follows. FIG. 2A illustrates a cleavage reaction catalyzed by exonuclease 106, wherein the polynucleotide substrate 202 is conjugated to an analog 204. The analog 204 is selected to bind with a preselected binding compound 208 and interfere with the cleavage reaction. In FIG. 2A, an exonuclease 206 is used in the cleavage reaction to cleave a double stranded polynucleotide 202 into a partially digested polynucleotide 212 and, finally, a single-stranded polynucleotide. In FIG. 2B, the binding compound 208 binds to the analog 204 and interferes with the cleavage reaction, such that the cleavage reaction is inhibited or quenched by the addition of the binding compound 208. In FIG. 1C, an analyte 210 that can also bind with the binding compound 208 competes with the analog 204 for binding to the binding compound 208. The competition for binding ties up a portion of the available binding compound 208 and, accordingly, results in a recuperation of the some of the cleavage reaction and production of the single-stranded polynucleotide 214. The amount of analyte present determines the amount of recuperation and, thus, the amount of recuperation provides a measure of the amount of analyte present.

Figure 3:
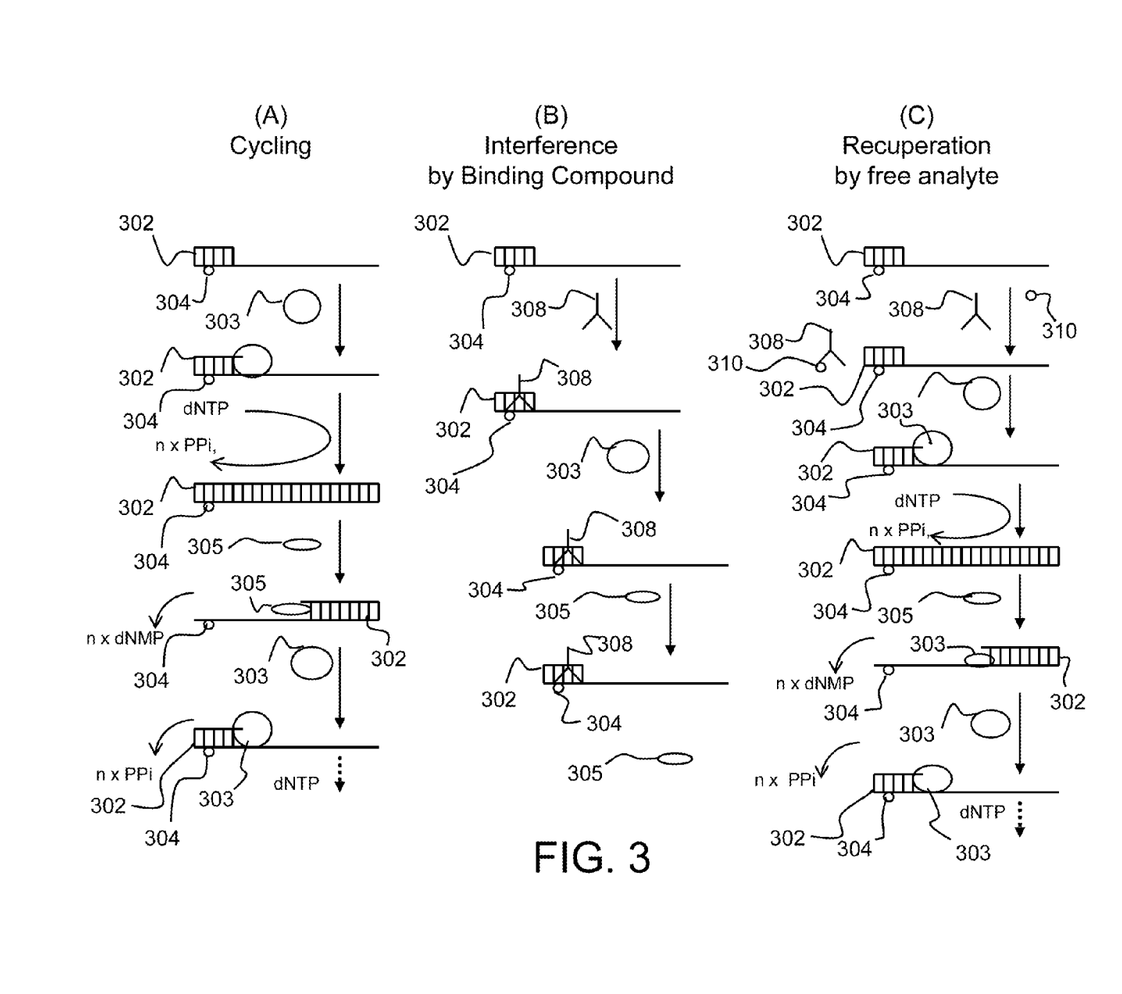
FIGS. 3A through 3C illustrate the principles of cycling of polymerase reaction interference and exonuclease interference and cycling recuperation, according to some embodiments.

FIGS. 3A through 3C illustrate the principles of cycling of polymerase reaction interference and exonuclease interference and cycling recuperation, according to some embodiments. Without intending to be bound by any theory or mechanism of action, the interference and recuperation activities of a cycling of polymerase and exonuclease reactions is believed to occur as follows. FIG. 3A illustrates a cycling reaction that includes polymerization of polynucleotide substrate 302 with polymerase 303 and cleavage with exonuclease 305. As in FIGS. 1 and 2, an analog 304 is selected to bind to a binding compound 308. In FIG. 3B, the binding compound 308 is shown to interfere with both stages of the cycling, both polymerization and cleavage. In FIG. 3C, an analyte 310 that can also bind with the binding compound 308 competes with the analog 304 for binding to the binding compound 308. The competition for binding ties up a portion of the available binding compound 308 and, accordingly, results in a recuperation of the some of the cleavage reactions and polymerization reactions, resulting in a cyclic growth of the polynucleotide substrate 302 into a double-stranded polynucleotide and digestion of the double stranded polynucleotide. The amount of analyte present determines the amount of recuperation and, thus, the amount of recuperation provides a measure of the amount of analyte present. The effect of the cycling is to increase sensitivity of the measurement by amplifying the measured signals, where the degree of amplification depends on the number of cycles used in the measurement.

Figure 4:
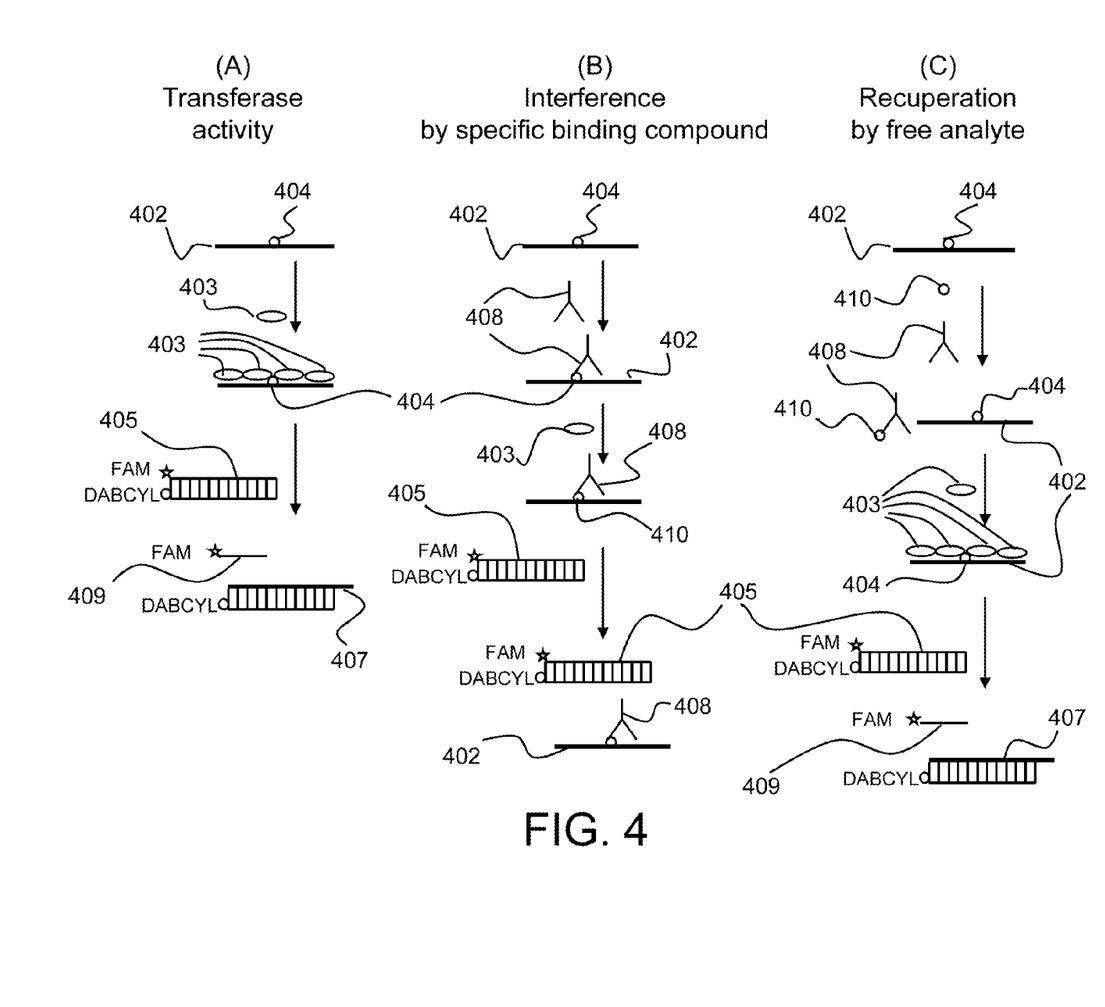
FIGS. 4A through 4C illustrate the principles of interference and recuperation of transferase activity, according to some embodiments.

FIGS. 4A through 4C illustrate the principles of interference and recuperation of transferase activity, according to some embodiments. Without intending to be bound by any theory or mechanism of action, the interference and recuperation of transferase activity is believed to occur as follows. FIG. 4A illustrates a polynucleotide substrate 402 that is a single-stranded polynucleotide. The single-stranded polynucleotide 402 is the target polynucleotide in this example. A transferase 403 and a probe double-stranded polynucleotide 405 are combined with the single-stranded target polynucleotide 402 to create a recombination reaction in which the target polynucleotide 403 replaces the FAM-labeled polynucleotide 409 to produce a recombined double-stranded polynucleotide 407. In FIG. 4B, the binding compound 408 binds to the analog 404 and interferes with the recombination reaction, such that the recombination reaction is inhibited or quenched by the addition of the binding compound 408. In FIG. 4C, an analyte 410 that can also bind with the binding compound 408 competes with the analog 404 for binding to the binding compound 408. The competition for binding ties up a portion of the available binding compound 408 and, accordingly, results in a recuperation of the some of the recombination reaction and production of the recombined double-stranded polynucleotide 407. The amount of analyte present determines the amount of recuperation and, thus, the amount of recuperation provides a measure of the amount of analyte present.

The teachings are generally directed to methods of measuring the concentration of an analyte in a solution, and the methods will include some form of the reactions discussed above. In some embodiments, the desired polynucleotide reaction comprises a nucleotide polymerization reaction, a nucleotide cleavage reaction, or a combination of a nucleotide polymerization reaction and a nucleotide cleavage reaction. In some embodiments, the desired polynucleotide reaction comprises a nucleotide recombination reaction. In some embodiments, the desired reaction provides a sensitivity that is significantly higher than currently available homogeneous phase assays through cycling of reactions, use of real-time PCR, use of polynucleotide substrates having sequences over 1 kb in length or longer, or combinations thereof.

The detection of the analyte can occur using the appearance or disappearance of a fluorescence signal generated from a chemical, such as a dye, that is bound to an oligonucleotide; or from an absorbance spectra, such as a UV-Visible spectral signal. In some embodiments, the detection includes recognizing a chemiluminescense signal generated from enzymatic coupling reactions. In some embodiments, the sensitivity of the measurements may be enhanced through the use of real-time PCR measurements. In some embodiments, a double-stranded polynucleotides can be detected using a chemical dye, for example, PICOGREEN. In some embodiments, a double-stranded probe is prelabeled with fluoresceine and darkquencher and, thus, can be used for transferase activity detection. In some embodiments, fluorescent resonance energy transfer (FRET) can be used for detection of the fluorescent signal. One of skill will appreciate that any of a number of known measurement systems can be used to complement the teachings provided herein.

The teachings provided herein are generally directed to a homogenous assay, in which the amount or presence of an analyte is measured without having to separate a fluid sample from other reaction components. A heterogenous assay is distinguishable from a homogeneous assay in that the reaction medium of the heterogeneous assay contains at least two separate phases, such as a solid support having reagents attached for binding to an analyte and a fluid medium containing analyte.

The methods include selecting a binding compound; selecting an analog to an analyte and conjugating the analog to a polynucleotide substrate to construct a reagent for measuring the amount of the analyte in an assay solution using a desired polynucleotide reaction. The binding of the reagent to the binding compound in the assay solution competes with the binding of the analyte to the binding compound in the assay solution.

One of skill will appreciate that an analyte can be any compound having an amount or presence to be determined in a fluid assay sample. Examples of analytes include, but are not limited to, toxins, controlled drug substances, hormones, small molecule pharmaceuticals, biopharmaceuticals, nucleic acids, proteins, peptides, immunoglobulins or their fragments, antigens, or bacterial or viral particles that can react with a ligand in a immunogenical mechanism or otherwise.

The selection of the binding compound depends on structure of the analyte that is being identified and/or quantified in a sample. For example, if the analyte is an antigen, an antibody to the antigen can serve as a good binding compound. If the analyte is a cytokine, for example, a cellular receptor can serve as a good binding compound for the cytokine. Accordingly, in some embodiments, the binding compound comprises a ligand binding molecule, an antibody, or a cellular receptor. Examples of such binding compounds can include, but are not limited to, immunoglobulin, vitamin binding protein, IL-1 receptors, T-cell receptors, and the like.

Selection of the binding compound will depend, at least in part, on the relative binding affinity of the binding compound for the analyte and the analog. A ligand binding molecule, for example, can include any molecule having a high binding affinity for another compound of interest. In some embodiments, the binding affinity ranges from about $1 \times 10^{-4}$ M to about $1 \times 10^{-8}$ M, from about $1 \times 10^{-5}$ M to about $1 \times 10^{-7}$ M, from about $5 \times 10^{-5}$ M to about $5 \times 10^{-6}$ M, and from about $8 \times 10^{-5}$ M to about $2 \times 10^{-6}$ M.

The selection of the analog also depends on the structure of the analyte that is being identified and/or quantified in a sample. In some embodiments, the analog comprises a structure of the analyte or is a compound having the molecular structure of the analyte. Conjugation of the analog to the substrate can be done using any method known to one of skill in the art. For example, the analog can be the analyte conjugated to a linker, and the linker is conjugated to the polynucleotide substrate. The analog, however, can be attached to the polynucleotide substrate with our without a linker, depending on the embodiment.

The selection of the polynucleotide substrate should correspond to the selection of the desired polynucleotide reaction, which can be a polymerization reaction, a cleavage reaction, a cycling of polymerization and cleavage, or a recombination reaction, for example. In some embodiments, the polynucleotide substrate comprises a polynucleotide primer, a polynucleotide template, or a combination thereof.

In some embodiments, the polynucleotide substrate is single-stranded or double-stranded. In some embodiments, the polynucleotide substrate is a double-stranded DNA or a single-stranded DNA. In some embodiments, the polynucleotide substrate can comprise RNA. In some embodiments, a polynucleotide can include a sequence of at least 10 nucleotides. In some embodiments, the polynucleotide substrate includes a sequence of at least 20 nucleotides, at least 30 nucleotides, at least 50 nucleotides, at least 75 nucleotides, at least 100 nucleotides, or at least 200 nucleotides. In fact, in some embodiments, the polynucleotide substrate can be much longer, having a length of at least 500 nucleotides, or even 1000 nucleotides or greater. In some embodiments, the polynucleotide substrate can include an initiation region, a promoter region or a combination thereof. The initiation region can comprise the sequence of nucleotides at which a polymerization reaction begins and may be on a single-stranded or a double-stranded polynucleotide. A promoter region can refer to a double-stranded initiation region and, in some embodiments, is formed by annealing an oligonucleotide or primer onto the initiation region of a single-stranded polynucleotide, wherein the oligonucleotide or primer is complementary to the intiation region.

One of skill in the art will understand how to create a polynucleotide substrate that is useful in polymerization reactions, cleavage reactions, or recombination reactions, as described herein. In some embodiments, the polynucleotide comprises at least 20 nucleotide residues, each residue comprising a purine or pyrimidine base, a sugar and a phosphate, and typically attached to other residues through a phosphodiester linkage. The nucleotides should have a sequence of nucleotides comprising an initiation region, as described herein. In some embodiments, the polynucleotide may be a double-stranded polynucleotide having a phage promoter, such as the T7 RNA polymerase promoter or the QB phage promoter. In some embodiments, the polynucleotide can a single-stranded polynucleotide containing an initiation region. A functional promoter region can be formed by annealing a short oligonucleotide primer to the initiation region to form a functional promoter. In some embodiments, the polynucleotide can contain sequences more than one promoter.

In some embodiments, the analog is linked to the polynucleotide through a linker. The linker should be selected to not substantially affect the desired polymerization, cleavage, or recombination reaction, and of course, it should not substantially affect the ability of the binding compound to bind to the analog. In some embodiments, biotin and/or avidin can be used as a linker.

The teachings set-forth herein provide a novel way for one of skill to measure the amount of an analyte that is present in any of a variety of assay solutions, such as fluid samples that are biological or non-biological. In some embodiments, the assays are immunoassays and, in some embodiments, the samples are serological. The samples can be a body fluid such as, for example, blood, blood serum, plasma, spinal fluid, semen, saliva, effusions, exudates, pus, amniotic fluid, urine, stool, fluid obtained from condensed lung exhalate or exudate, cell tissue, and the like. In some embodiments, the fluid sample can be a culture mediums, samples of pharmacological agents, food samples, dairy products, water samples, and the like. In some embodiments, the sample can be a sample of an industrial fluid.

In some embodiments, the teachings provided herein can be used to detect analytes that are currently tested by heterogenous systems, including immunogenic analyst such as antibodies, or non-immunogenic analytes, such as glycoproteins. For example, a T-cell receptor, such as CD4, may be used as the binding compound for an antibody against HIV. Or, as another example, a lectin that recognizes a polysaccharide on a glycoprotein could be used as a binding compound for the glycoprotein.

The teachings provided herein can be used to measure the concentration of Vitamin D3 in a sample. Vitamin D3 is a pre-hormone that has long been known for its important role in regulating body levels of calcium and phosphorus, as well as in mineralization of bone. Clinical applications in the rapidly expanding field of Vitamin D3 research have to a great extent been limited by the methodologies used and, as such, one of skill will appreciate having the ability to measure Vitamin D3 levels using the methods taught herein. In some embodiments, the analyte can be Vitamin D3; the analog can comprise Vitamin D3, or a derivative thereof, and can be conjugated to a polynucleotide to make the assay reagent; and, an anti-Vitamin D3 antibody can be used as the binding compound. Klenow DNA polymerase can be selected for the enzyme reaction. When the anti-Vitamin D3 antibody binds to the reagent, it will block the Klenow enzyme activity. The free Vitamin D3 in sample will recuperate the Klenow enzyme activity by competitively binding to the anti-Vitamin D3 antibody, and the amount of recuperation in Klenow enzyme activity will provide a measure of the Vitamin D3 in the sample.

Drug abuse is a major problem in our society and, accordingly, improvements in the methods of measuring drug levels easily, accurately, and precisely are appreciated those of skill. Currently, however, this field still uses heterogenous assays and would benefit from the methods taught herein. The teachings provided herein can be used in detecting cocaine, for example. In some embodiments, the analyte can be cocaine; the analog can comprise cocaine or a derivative thereof, and can be conjugated to a polynucleotide to make the assay reagent; and, an anti-cocaine antibody can be used as the binding compound. Klenow DNA polymerase can be selected for the enzyme reaction. The Cocaine from a sample will competitively binding to the anti-Cocaine antibody. The recuperated activity of the Klenow is correspond to the Cocaine's concentration in the sample. When the anti-cocaine antibody binds to the reagent, it will block the Klenow enzyme activity. The free cocaine in the sample will recuperate the Klenow enzyme activity by competitively binding to the anti-cocaine antibody, and the amount of recuperation in Klenow enzyme activity will provide a measure of the cocaine in the sample.

Analytes having a larger molecular size are also easily measured using the methods provided herein. Brain natriuretic peptide (BNP) and proBNP, for example, are useful in the assessment of heart failure, left ventricular dysfunction, and acute coronary syndromes. The proBNP is an important cardiac marker for heart disease and, an easy to use, accurate, and precise method of measuring proBNP would be appreciated by those of skill. In some embodiments the analyte is proBNP, an anti-proBNP monoclonal antibody can be used as the binding compound. And, the analog can comprise an epitope of the proBNP, a peptide that is recognized by the anti-proBNP antibody, and can be conjugated to a polynucleotide to generate the reagent. Klenow DNA polymerase can be selected for the enzyme reaction. When the anti-proBNP antibody binds to the reagent, it will block the Klenow enzyme activity. The free proBNP in the sample also contains the epitope and will recuperate the Klenow enzyme activity by competitively binding to the anti-proBNP antibody, and the amount of recuperation in Klenow enzyme activity will provide a measure of the proBNP in the sample.

Industrial samples can also contain analytes of interest and, as such, the methods taught herein can be applicable for use with industrial samples. In an environmental study, for example, the weathered oils in a contaminated soil sample can also be measurement with the new invent. The solvent extractable matter (SEM) can be used to immunize and create antibodies in an animal, such that an anti-SEM antibody is created. In some embodiments, the analyte is SEM, the analog can comprise SEM and can be conjugated to a polynucleotide to generate the reagent. Klenow DNA polymerase can be selected for the enzyme reaction. When the anti-SEM antibody binds to the reagent, it will block the Klenow enzyme activity. The free SEM in the sample will recuperate the Klenow enzyme activity by competitively binding to the anti-SEM antibody, and the amount of recuperation in Klenow enzyme activity will provide a measure of the SEM in the sample.

BIOTIN (Vitamin H or B7) is a small molecule that binds to avidin, a tetrameric protein, with a high affinity. As such, BIOTIN is commonly used for labeling compounds for binding with avidin. In some embodiments, any of a variety of analytes can be labeled with BIOTIN and quantitatively measured using the methods taught herein. A BIOTIN labeled compound can be selected as an analyte, and the analog can comprise BIOTIN and can be conjugated to a polynucleotide to form the reagent. Avidin can be used as the binding compound, and Klenow DNA polymerase can be selected for the enzyme reaction. When the avidin binds to the reagent, it will block the Klenow enzyme activity. The free BIOTIN-labeled analyte in the sample will recuperate the Klenow enzyme activity by competitively binding to the avidin, and the amount of recuperation in Klenow enzyme activity will provide a measure of the analyte in the sample.

After the components have been selected and constructed for a particular use, the relative amounts of the components can be selected top optimize use of the method. Optimizing use of the methods includes determining a desired ratio of the binding compound to the reagent for a given concentration of the analyte in the assay solution. This step includes providing a preselected amount of the desired enzyme to catalyze the desired reaction. The desired amount and type of enzyme is selected by determining a desired reaction kinetics. Examples of enzymes include, but are not limited to, polymerases, such as DNA polymerases and RNA polymerases; nucleases, such as exonucleases; transferases, such as RecA, RadA, Rad51, and the like, wherein the enzyme can use an oligonucleotide as a substrate.

A series of binding compound concentrations are constructed to determine the desired ratio of binding compound to reagent. The range of binding compound concentrations selected is based on an expected range of analyte concentrations. Each of the test samples are based on each of the binding compound concentrations, respectively, and includes a fixed amount of enzyme, and a fixed amount of reagent. In some embodiments, the fixed amount of reagent, for example, may be an equimolar amount of the reagent to the expect amount of analyte. The amount or reagent used may depend, in some embodiments, on how well the reagent competes with the analyte for the binding compound.

Once the desired ratio of binding compound to reagent has been determined for an expected range of analyte concentration, the desired ratio of the binding compound to the reagent can be fixed, and an analyte-concentration calibration curve developed, for use in measuring the activity of the desired enzyme during the desired polynucleotide reaction. The analyte-concentration calibration curve can be based on a series of solutions having a series of analyte concentrations over the expected range, a fixed amount of a desired enzyme, and fixed amounts of binding compound and reagent in the desired ratio. The analyte-concentration calibration curve can be used to determine the amount of an analyte in an assay solution.

After creation of an analyte concentration calibration curve, an assay solution is created and contains the analyte to be measured and an amount of the binding compound. An amount of the reagent is then added to the assay solution to provide the desired ratio of the binding compound to the reagent. The preselected amount of the desired enzyme is then added to the assay solution to catalyze the desired polynucleotide reaction. The activity of the desired enzyme is then measured during the desired polynucleotide reaction to determine the amount of the analyte in the assay solution using the analyte-concentration calibration curve.

In some embodiments, the teachings are directed to a reagent for a competitive binding assay. The reagent can comprise a polynucleotide substrate conjugated to an analog, and the analog can be selected to (i) bind to a preselected binding compound in an assay solution; and (ii) compete with a binding of an analyte to the preselected binding compound in the assay solution. The polynucleotide substrate can be selected to participate in a desired polynucleotide reaction that is inhibited or quenched by the binding of the binding compound to the analog in the assay solution.

In some embodiments, the teachings are directed to a competitive assay binding kit for measuring the amount of an analyte in an assay solution. The kit comprises the reagent described above, as well as a binding compound for use in a competitive binding assay, wherein the binding of the reagent to the binding compound in an assay solution competes with the binding of an analyte to the binding compound in the assay solution. The kit also includes an enzyme for catalyzing a desired polynucleotide reaction, wherein the activity of the enzyme is measured to determine the amount of the analyte in the assay solution.

Example 1

Using an Anti-Analyte Antibody to Interfere with Polymerization in a Polymerase Reaction This example shows how anti-analyte antibody can be used as a binding molecule to intentionally interfere with polymerization in a polymerase reaction in a dose-dependent manner. The binding molecule is selected to bind to an analog that is attached to the DNA template, primer, or both, and the binding of the binding molecule to the analog interferes with the polymerase reaction.

A DNA template was chosen for use in the polymerase reaction. The chosen DNA template was the following 51 mer single-stranded oligonucleotide:

```
                                       (SEQ ID NO: 7)
5'-ACCAACACCACACACAACCAACACACACCAACCACAACACCACCATG

TCTC-3'
```

A primer sequence was also chosen for use in the reaction. The primer sequence was the following oligonucleotide:

```
    5'-GAGACAUGG-3'            (SEQ ID NO: 4)
```

The analog was attached to the primer in this example. The uracil (U) was conjugated with the analog using methods known to those of skill in the art. The analog chosen was Digoxigenin (Dig) (Chevalier J. at. al. 1907). And, as described above, the conjugation of the Dig to the primer was performed to construct a reagent having a binding site for the binding molecule. An anti-Dig antibody Fab fragment (Roche Diagnostics, Germany) was chosen as the binding molecule in this example.

A 50 μL reaction mixture containing 10 mM Tris-HCl (pH 7.9), 50 mM NaCl, 10 mM $MgCl_2$, 2.5 nmol of each dNTP, 17 nM of template/primer oligonucleotides and 1:200 diluted PICOGREEN (Invitrogen, San Diego) was created. The Fab fragment was added to the reaction mixture in a series of concentrations and included 5 nM, 10 nM, 20 nM, 40 nM, 80 nM, 160 nM, and 320 nM concentrations. The reaction mixture was incubated at room temperature for 5 minutes, and then 1 unit of DNA polymerase, Klenow (New England BioLabs, Ipswich, Mass., USA), was added to initiate the polymerase reaction. After an additional 5 minutes of incubation, the double stranded DNA generated from the DNA polymerase reaction was detected by the fluorescence generation. The fluorescence signal was measured at 520 nm using an excitation wavelength of 480 nm (Wittwer, C. T., et. Al 1997a).

The anti-Dig antibody significantly inhibited the DNA polymerase chain reaction in a dose-dependent manner. During the formation of the double strand DNA, pyrophosphate (PPi), a byproduct of the polymerase reaction, was accumulated. The amount of PPi generated was measured to determine the extent of the reaction according to the following principle:

(1)
(2)

The enzyme, inorganic pyrophosphatase, which catalyzes conversion of PPi into two equivalents of Pi, can be used to amplify the measurement and gain measurement sensitivity, since one molecule of PPi becomes two molecules of Pi. The cleaved inorganic phosphate (Pi) is reacted with 2-amino-6-mercapto-7-methylpurine ribonucleoside (MESG) and enzymatically catalyzed by purine nucleoside phosphorylase (PNP) to form ribose 1-phosphate and 2-amino-6-mercapto-7-methylpurine. Enzymatic conversion of MESG results in a shift in an absorbance maximum, wherein the absorbance maximum shifts from 330 nm for the substrate to 360 nm for the product. The assay can detect as little as 1 nanomole of PPi in 1 mL reaction mixtures and can be performed within a pH range of 6.5 to 8.5.

The inorganic phosphate (Pi) released was also detected as following:

(1)
(2)
(3)

wherein, the NAD(P)H generated was monitored at 340 nm.

Example 2

Using the Interference of Polymerization by an Anti-Analyte Antibody in a Polymerase Reaction to Detect the Concentration of an Analyte in a Sample The conditions and materials taught in Example 1 were used in this example, unless otherwise specified. Example 1 showed how an anti-analyte antibody can interfere with the polymerization in a polymerase reaction and does so in a dose-dependent manner. This example shows how the interference can be used in the presence of an analyte to detect the concentration of the analyte in a sample.

A 50 µL reaction mixture containing 10 mM Tris-HCl (pH 7.9), 50 mM NaCl, 10 mM $MgCl_2$, 2.5 nmol of each dNTP, 1:200 diluted PICOGREEN (Invitrogen, San Diego) and 33 nM of anti-Dig antibody Fab fragment (Roche Diagnostics, Germany) was created. An analyte was selected to test the competitive binding analyte measurement technique. Dig was chosen as the analyte, and samples having different Dig analyte concentrations were added to the reaction mixture to compete with the Dig analog for binding to the antibody. The highest concentration of Dig used in this example was 1600 nm.

As described above, the analog to the Dig analyte was also Dig, wherein the Dig conjugated to the uracil nucleotide of the primer for purposes of competing with the Dig analyte for binding to the antibody binding molecule. A 17 nM concentration of template/primer oligonucleotides was combined with 1 unit of DNA polymerase, Klenow, to initiate the polymerase reaction.

Figure 5:
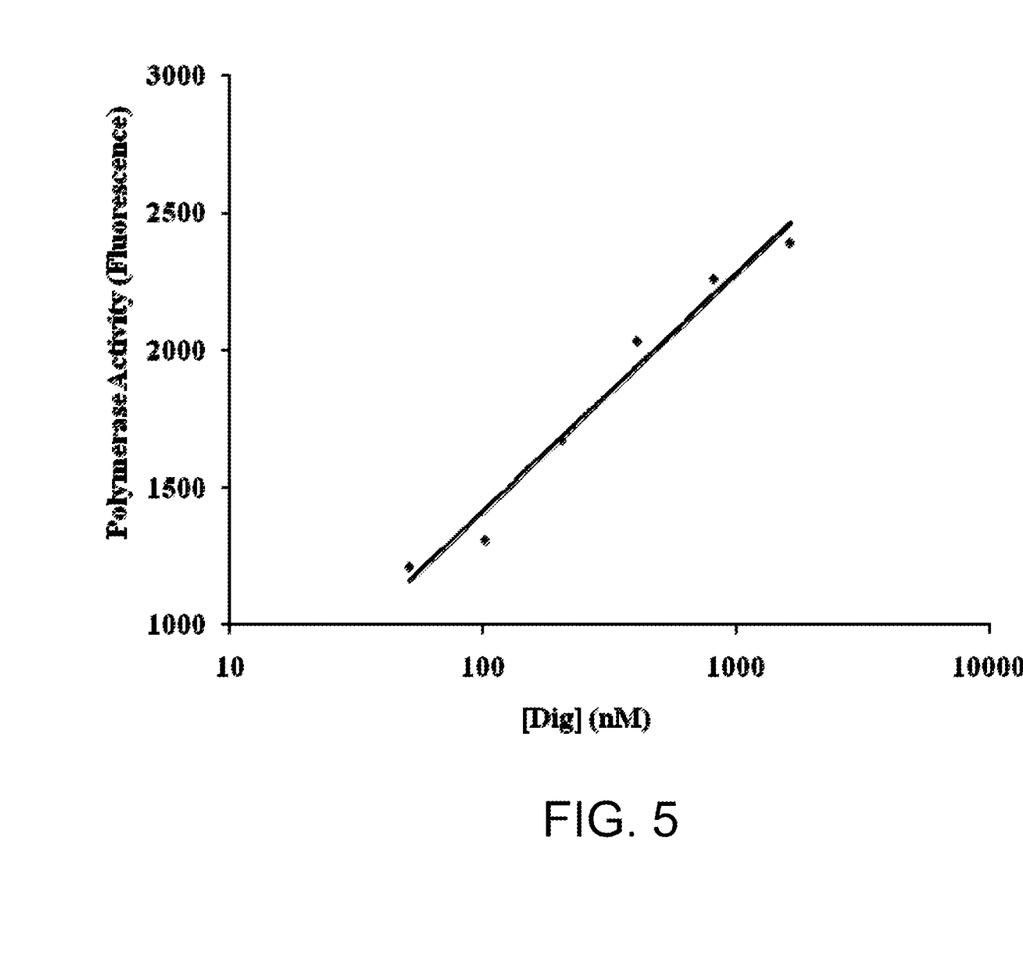
FIG. 5 illustrates a competitive binding assay using polymerase reaction interference, according to some embodiments.

FIG. 5 illustrates a competitive binding assay using polymerase reaction interference, according to some embodiments. As shown in the FIG. 5, as the concentration of the analyte Dig increases, the DNA polymerase activity increases, as did the corresponding fluorescence of the PICOGREEN. Accordingly, this result shows how the concentration of analyte, which in this example is Dig, can be measured through a competitive binding assay that includes a polymerase reaction interference and recuperation technique.

Example 3

Using an Anti-Analyte Antibody to Interfere with Cleavage in an Exonuclease Reaction Examples 1 and 2 describe how the competitive binding assay can be used to measure the concentration of analyte by interfering with a polymerization reaction using an anti-analyte antibody. This example uses an anti-analyte antibody to interfere with an exonuclease cleavage reaction to measure the amount of analyte in a sample.

The substrate to be cleaved in the exonuclease reaction is the following double stranded DNA (dsDNA) fragment:

The sense sequence is (SEQ ID NO: 5)
5'-ACCAACACCACACACAACCAACACACACCAACCACAACACCACCATG TCTCTCTGAC-3' and was labeled with Dig at the 3' end of the sequence as an analog to the analyte, wherein the analog with compete with the analyte for binding to a binding molecule.

The anti-sense sequence is (SEQ ID NO: 1)
5'-GTCAGAGAGACATGGTGGTGTTGTGGTTGGTGTGTGTTGGTTGTGTG TGGTGTTGGT-3'

A 90 µL reaction mixture containing 67 mM glycine-KCl (pH 9.4), 2.5 mM MgCl$_2$, 50 ug/mL BSA, 10 nM of Dig conjugated dsDNA, and 1:200 diluted PICOGREEN (Invitrogen, San Diego) was created. An anti-Dig antibody Fab fragment (Roche Diagnostics, Germany) was added to the reaction mixture in a series of concentrations and included 5 nM, 10 nM, 20 nM, 40 nM, 80 nM, 160 nM, and 320 nM concentrations.

The reaction mixture incubated at room temperature for 5 minutes, and then 2.5 unit of λ-exonuclease (New England BioLabs, Ipswich, Mass., USA) was added to initiate the cleavage reaction and selectively hydrolyze the dsDNA from the 5' end and create a ssDNA (Tolun, G. and Myers, R. S. 2003). After an additional 5 minutes of incubation, the exonuclease activity was detected by fluorescence measurements, where a digested dsDNA was shown to exhibit a progressive disappearance of fluorescence. In the presence of the binding molecule, the anti-Dig antibody Fab fragment, the fluorescence signal remained strong, indicating that anti-Dig antibody interfered with the activity of the λ-exonuclease, and it did so in dose-dependent manner.

Example 4

Using the Interference of Cleavage by an Anti-Analyte Antibody in an Exonuclease Reaction to Detect the Concentration of an Analyte in a Sample The conditions and materials taught in Example 3 were used in this example, unless otherwise specified. Example 3 showed how an anti-analyte antibody can interfere with the cleavage of a dsDNA in an exonuclease reaction and does so in a dose-dependent manner. This example shows how the interference can be used in the presence of an analyte to detect the concentration of the analyte in a sample.

In this example, the anti-Dig antibody described above was mixed with a Dig analyte first to allow the analyte to tie-up the antibody to an extent corresponding to the analyte's concentration, leaving the reagent free to react with the exonuclease to the extent that reagent is not bound to the antibody. The reagent in this case is the dsDNA conjugated to the Dig analog. The antibody concentration was fixed, and the analyte was added at varying concentrations. The highest concentration of Dig used in this example was 960 nm.

As the analyte concentration decreased, the amount of free reagent subject to cleavage by the exonuclease reaction also decreased. the fluorescence detection using PICOGREEN was a measure of the change in exonuclease activity and, thus, analyte concentration.

Figure 6:
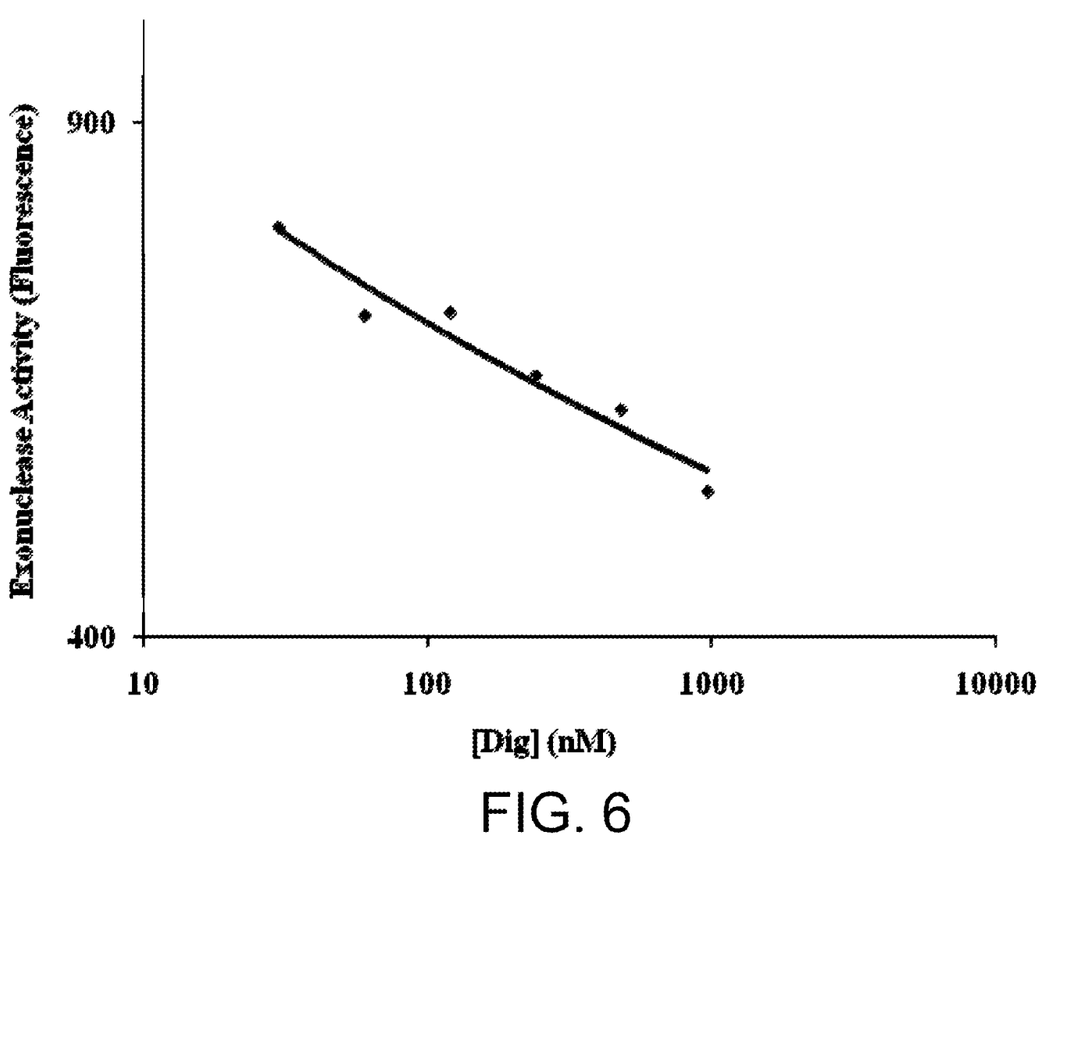
FIG. 6 illustrates a competitive binding assay using exonuclease reaction interference, according to some embodiments.

FIG. 6 illustrates a competitive binding assay using exonuclease reaction interference, according to some embodiments. As shown in the FIG. 6, as the concentration of the analyte Dig increases, so did the exonuclease activity, as evidenced by the corresponding decrease in fluorescence of the PICOGREEN. As shown in the FIG. 6, the concentration of analyte, which in this example is Dig, can be measured through a competitive binding assay that includes an exonuclease reaction interference and recuperation technique.

Alternatively, the exonuclease reaction activity, and thus analyte concentration, can also be monitored by using dNMP (the other products of the λ-exonuclease reaction) dehydrogenase coupling with NADH or NADPH.

Example 5

Cycling a Combination of Polymerase-Exonuclease Reaction Interferences to Amplify the Detection Signal and Measure Smaller Concentrations of an Analyte in a Sample Examples 2 and 4 above uses a signal detected from either the process of interfering with the polymerization in a polymerase reaction or the process of interfering with cleavage in an exonuclease reaction to determine the concentration of analyte in a sample. This example shows that a cycling of (i) the interference of polymerization by an anti-analyte antibody in a polymerase reaction and (ii) the interference of cleavage by an anti-analyte antibody in an exonuclease reaction can be used to significantly amplify signal detection and measure the concentration of an analyte in a sample with an even higher degree of sensitivity.

As such, this experiment shows that DNA polymerase and λ-exonuclease can be combined to generate a cycling assay that significantly amplifies the detection signal for measuring the concentration of an analyte in sample, allowing the detection of even lower concentrations of analyte. The conditions and materials taught in Example 1 were used in this example, unless otherwise specified.

1 unit of polymerase and 2.5 units λ-exonuclease were added simultaneously to the reaction mixture. The synthesized dsDNA by the DNA polymerase was digested and removed from the DNA template by the λ-exonuclease and multiple copies of pyrophosphate (PPi), dAMP, dCMP, dGMP, dTMP, were generated. The released PPi and dNMPs were detected by a PPi assay and a mononucleotide assay, respectively, amplifying the detection signal multiple times.

In the absence of Dig analyte, the anti-Dig antibody inhibited the DNA polymerase activity. As the Dig analyte was added, the polymerase and λ-exonuclease activities increased. Accordingly, this example illustrated that the amount of Dig analyte in the sample was proportional to the signal detected using a PPi assay and a mononucleotide assay.

Example 6

Using an Anti-Analyte Antibody to Interfere with a Recombination in a Transferase Reaction Examples 2 and 4 above show how interference of polymerization or cleavage reactions can affect enzyme activity and produce a signal that provides a measure of analyte in a sample. This example shows how the interference of recombination by an anti-analyte antibody in a transferase reaction can be used to detect the concentration of an analyte in a sample.

A double-stranded proble and a single-stranded target were selected for use in the recombination reaction. The double-stranded DNA probe sequence had the following structure:

```
                                            (SEQ ID NO: 3)
5'FAM-AAACTAATAAGATTTACA-ACAATTTCTC-3';
and (SEQ ID NO: 2)
3'-DABYL-TTTGATTATTCT-AAATGTTGTTAAAGAG-5'
```

The single-stranded target had the same sequence as the 5' FAM oligonucleotide: 5'-AAACTAATAAGATTTACAA-CAATTTCTC-3' (SEQ ID NO:6), however this ssDNA was the polynucleotide that was conjugated with an analog to provide a site for binding with the binding molecule and interfering with the recombination reaction, the transferase reaction. In this example, the $T^{14}$ was conjugated with a Dig molecule.

A 60 µl of reaction mixture containing 70 mM Tris-HCl, (pH 7.6), 12 mM $MgCl_2$, 0.3 mM ATP, (ATP regenerating system may also need 3 mM phosphoenolpyruvate and 30 U/ml pyruvates kinase), 4.5 uM (in nucleotides) target single stranded Dig-DNA, 3 uM RecA (New England BioLabs, Ipswich, Mass., USA) was created. An anti-Dig antibody Fab fragment (Roche Diagnostics, Germany) was added to the reaction mixture in a series of concentrations that included 5 nm, 10 nm, 20 nM, 40 nM, 80 nM, 160 nM, and 320 nM concentrations.

The reaction mixture incubated for 3 minutes at 37° C. to allow for binding between the antibody and the analog that was conjugated to the single-stranded target. 4.5 uM (in nucleotides) of the double-stranded probe DNA was then added to the reaction mixture.

After an additional 3 minutes of incubation at 37° C., a fluorescence signal was generated by exchanging the FAM-labeled 5'-sequence in the double stranded DNA with the FAM-free 5'-target single stranded DNA target sequence which is catalyzed by RecA DNA transferase. The fluorescence signal was monitored at 520 nm with excitation wavelengths of 490 nm. In the presence of the binding molecule, the anti-Dig antibody Fab fragment, the fluorescence signal decreased, indicating that the anti-Dig antibody interfered with the activity of the transferase, RecA, and it did so in a dose-dependent manner.

Example 7

Using the Interference of Recombination by an Anti-Analyte Antibody in an Transferase Reaction to Detect the Concentration of an Analyte in a Sample The conditions and materials taught in Example 6 were used in this example, unless otherwise specified. Example 6 showed how an anti-analyte antibody can interfere with the recombination reaction between a dsDNA probe and a ssDNA target sequence in a transferase reaction and do so in a dose-dependent manner. This example shows how the interference can be used in the presence of an analyte to detect the concentration of the analyte in a sample Dig was chosen as the analyte, and samples having different Dig analyte concentrations were added to the reaction mixture to compete with the Dig analog for binding to the antibody. The highest concentration of Dig used in this example was 650 nm.

The anti-Dig antibody described above was mixed with a Dig analyte first to allow the analyte to tie-up the antibody to an extent corresponding to the analyte's concentration, leaving the reagent free to react with the transferase to the extent that reagent is not bound to the antibody. The reagent in this case is the ssDNA conjugated to the Dig analog. The antibody concentration was fixed, and as the analyte concentration was decreased, the amount of free reagent subject to recombination by the RecA transferase reaction also decreased, and the fluorescence detection at 520 nm was a measure of the change in transferase activity and, thus, analyte concentration.

Figure 7:
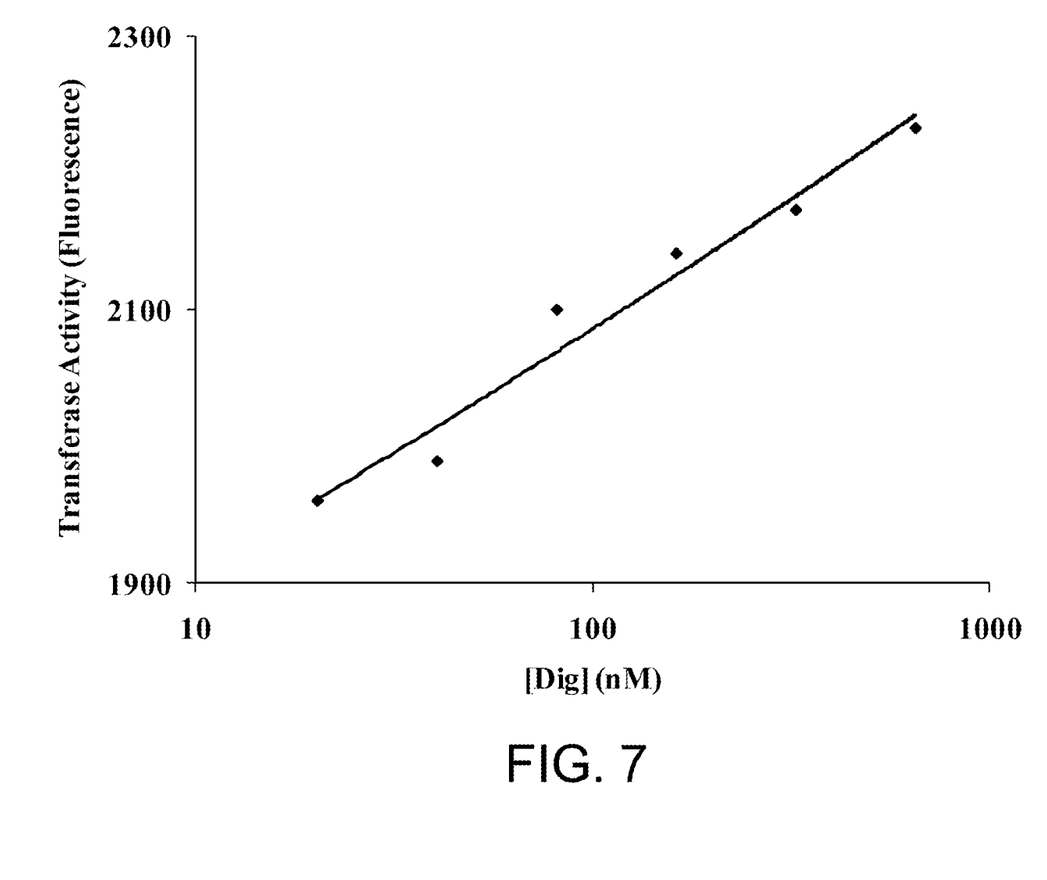
FIG. 7 illustrates a competitive binding assay using transferase reaction interference, according to some embodiments.

FIG. 7 illustrates a competitive binding assay using transferase reaction interference, according to some embodiments. As shown in the FIG. 7, as the concentration of the analyte Dig increases, the transferase activity increases, as did the corresponding fluorescence at 520 nm. Accordingly, the concentration of analyte, which in this example is Dig, can be measured through a competitive binding assay that includes, in this example, a RecA transferase reaction interference and recuperation technique.

Example 8

Using an Anti-Analyte Antibody to Interfere with Polymerization in a Polymerase Reaction—Measuring Result by Product Yield Rather than Fluorescence or Absorbance The conditions and materials used in Example 1 were used in this example, unless otherwise specified. Examples 1 through 7 prove that polymerase activity, exonuclease activity, or transferase activity can be measured and used to determine the amount of an analyte in a sample. The measurements used to correlate with an analyte concentration in the examples have included the fluorescence of PICOGREEN and UV absorbance. Real-time quantitive PCR can also be used to increase the sensitivity and precision of the measurement.

The PCR primers are designed base on the new synthesized DNA chain. They only detect the new synthesized DNA. In this example, the enzyme activity is correlated to the free substrate labeled with a Dig analog or the concentration of the anti-Dig antibody. A 25 µL reaction mixture containing 10 mM Tris-HCl (pH 7.9), 50 mM NaCl, 10 mM $MgCl_2$, 1 mM DTT, 2.5 nmol of each dNTP, 1 unit Klenow DNA polymerase, 1.25 unit Taq DNA polymerase, 0.1 nM DNA template/Dig conjugated primer mixture and 200 nM each PCR primers is created. The concentration of the antibody Fab fragment (Roche Diagnostics, Germany) was provided at varying concentrations, the highest concentration of which was 666 nM and the lowest being about 10 nM.

Figure 8:
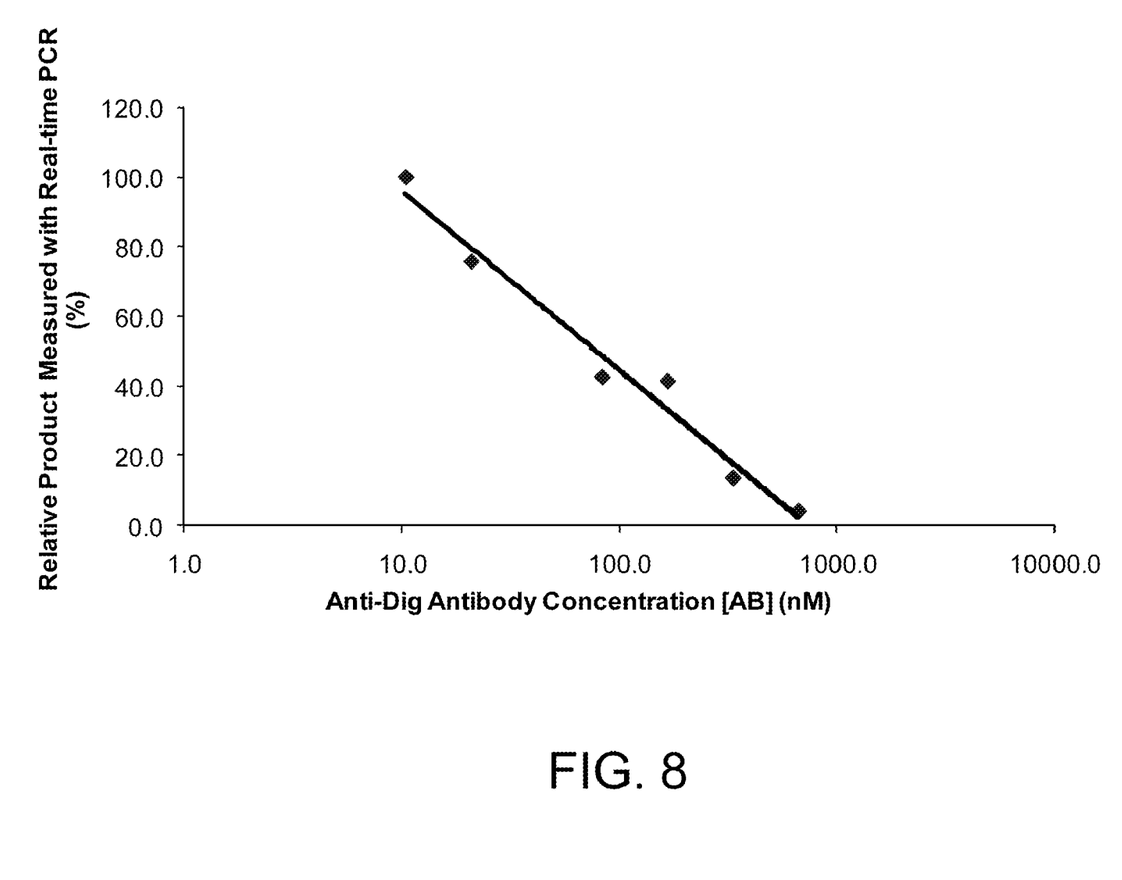
FIG. 8 illustrates how real-time PCR can be used to measure the anti-Dig antibody interference of a polymerase reaction, according to some embodiments

FIG. 8 illustrates how real-time PCR can be used to measure the anti-Dig antibody interference of a polymerase reaction, according to some embodiments. As shown in the FIG. 8, as the concentration of the binding compound (anti-Dig Fab fragment, [AB]) increases, the polymerase activity decreases, as determined using real-time PCR measurements. The real-time PCR provided a measure of the relative polymerization product formed, where 100% relative product should correspond to no antibody in the reaction mixture. A decrease in the relative polymerization product corresponds to an increase in the amount of antibody, or binding compound, that was added. Note that real-time PCR provides a very sensitive measure, and as such, only 0.1 nM of the polynucleotide substrate was used. At this concentration, 10 nM of the antibody had little effect. Accordingly, real-time PCR is another measurement that can be used to measure the activity of any of the enzymes taught above with greater sensitivity, precision and accuracy in the determination of an amount of analyte in a sample.

Those skilled in the art will recognize, or be able to ascertain using no more than routine experimentation, that there are many equivalents to the specific embodiments described herein that have been described. One of skill can practice the concepts taught herein well-beyond the scope of the specified embodiments. Such equivalents are intended to be encompassed by the following claims. In addition, there are numerous lists and groups taught and claimed herein. One of skill will appreciate that each such list and group contains various species and can be modified by the removal, or addition, of one or more of species, since every list and group taught and claimed herein may not be applicable to every embodiment feasible in the practice of the invention.

I claim:

1. A method of measuring the concentration of an analyte in a solution through interference and recuperation of a polymerization reaction, wherein the method comprises:

selecting a polynucleotide primer and a polynucleotide template, wherein the primer comprises an initiation region and anneals to the template for a polynucleotide polymerization reaction;

selecting a binding compound;

selecting an analog to an analyte and conjugating the analog to the polynucleotide primer or the polynucleotide template to construct a reagent for measuring the amount of the analyte in an assay solution using the polynucleotide polymerization reaction; wherein, the binding of the reagent to the binding compound in the assay solution competes with the binding of the analyte to the binding compound in the assay solution;

selecting a polymerase for catalyzing the polynucleotide polymerization reaction;

determining a desired ratio of the binding compound to the reagent for a given concentration of the analyte in the assay solution and a preselected amount of the polymerase;

creating an assay solution containing an amount of the binding compound and the analyte in the amount to be measured;

adding an amount of the reagent to the assay solution, wherein the amount of the reagent and the amount of the binding compound provides the desired ratio of the binding compound to the reagent;

adding the preselected amount of the polymerase to the assay solution to catalyze the polynucleotide polymerization reaction; and measuring the activity of the polymerase during the polynucleotide polymerization to determine the amount of the analyte in the assay solution;

wherein, the analog does not block the annealing of the primer to the template, blocks the polymerization reaction following the annealing, and a recuperation of the reaction provides the activity of the polymerase, and the measured activity of the polymerase provides a measure of the amount of analyte present.

2. The method of claim 1, wherein the binding compound comprises a ligand binding molecule.

3. The method of claim 1, wherein the binding compound comprises an antibody.

4. The method of claim 1, wherein the binding compound comprises a cellular receptor.

5. The method of claim 1, wherein the analog comprises a structure of the analyte.

6. The method of claim 1, wherein the analog is a compound having the molecular structure of the analyte.

7. The method of claim 1, wherein the polynucleotide substrate comprises a polynucleotide primer, a polynucleotide template, or a combination thereof.

8. The method of claim 1, wherein the polynucleotide substrate is a single-stranded DNA.

9. A method of measuring the concentration of an analyte in a solution through interference and recuperation of a cleavage reaction, wherein the method comprises:

selecting a double-stranded DNA for a polynucleotide cleavage reaction;

selecting a binding compound; and, selecting an analog to an analyte and conjugating the analog to the double-stranded DNA to construct a reagent for measuring the amount of the analyte in an assay solution using a polynucleotide cleavage reaction; and wherein, the binding of the reagent to the binding compound in the assay solution competes with the binding of the analyte to the binding compound in the assay solution;

selecting an exonuclease for catalyzing the cleavage reaction;

determining a desired ratio of the binding compound to the reagent for a given concentration of the analyte in the assay solution and a preselected amount of the exonuclease;

creating an assay solution containing an amount of the binding compound and the analyte in the amount to be measured;

adding an amount of the reagent to the assay solution, wherein the amount of the reagent and the amount of the binding compound provides the desired ratio of the binding compound to the reagent;

adding the preselected amount of the exonuclease to the assay solution to catalyze the cleavage reaction; and measuring the activity of the exonuclease during the polynucleotide cleavage to determine the amount of the analyte in the assay solution;

wherein, a recuperation of the cleavage reaction provides the activity of the exonuclease, and the measured activity of the exonuclease provides a measure of the amount of analyte present.

10. The method of claim 9, wherein the binding compound comprises a ligand binding molecule.

11. The method of claim 9, wherein the binding compound comprises an antibody.

12. The method of claim 9, wherein the binding compound comprises a cellular receptor.

13. The method of claim 9, wherein the analog comprises a structure of the analyte.

14. The method of claim 9, wherein the analog is a compound having the molecular structure of the analyte.

15. The method of claim 9, wherein the polynucleotide substrate is a double-stranded DNA.

16. The method of claim 1, wherein the method further comprises:

selecting an exonuclease for catalyzing a polynucleotide cleavage reaction; and, cycling the polynucleotide polymerization and cleavage reactions; wherein, a recuperation of both the polymerization and cleavage reaction during the cycling provides (i) a measured combined recuperation activity of both the polymerase and the exonuclease, and (ii) an amplification of the sensitivity of the method.

17. The method of claim 9, wherein the method further comprises:

selecting a polymerase for catalyzing a polynucleotide polymerization reaction; and, cycling the polynucleotide polymerization and cleavage reactions; wherein, a recuperation of both the polymerization and cleavage reaction during the cycling provides (i) a measured combined recuperation activity of both the polymerase and the exonuclease, and (ii) an amplification of the sensitivity of the method.

18. A method of measuring the concentration of an analyte in a solution through interference and recuperation of a recombination reaction, wherein the method comprises:

selecting a single-stranded target polynucleotide and a double-stranded DNA probe;

selecting a binding compound;

selecting an analog to an analyte and conjugating the analog to the target polynucleotide to construct a reagent for measuring the amount of the analyte in an assay solution using a polynucleotide recombination reaction; and wherein, the binding of the reagent to the binding compound in the assay solution competes with the binding of the analyte to the binding compound in the assay solution;

selecting a transferase for catalyzing the recombination reaction;

determining a desired ratio of the binding compound to the reagent for a given concentration of the analyte in the assay solution and a preselected amount of the transferase;

creating an assay solution containing an amount of the binding compound and the analyte in the amount to be measured;

adding an amount of the reagent to the assay solution, wherein the amount of the reagent and the amount of the binding compound provides the desired ratio of the binding compound to the reagent;

adding the preselected amount of the transferase to the assay solution to catalyze the recombination reaction; and measuring the activity of the transferase during the polynucleotide cleavage to determine the amount of the analyte in the assay solution;

wherein, a recuperation of the recombination reaction provides the activity of the transferase, and the measured activity of the transferase provides a measure of the amount of analyte present.

19. The method of claim 18, wherein the binding compound comprises a ligand binding molecule.

20. The method of claim 18, wherein the binding compound comprises an antibody.

21. The method of claim 18, wherein the binding compound comprises a cellular receptor.

22. The method of claim 18, wherein the analog comprises a structure of the analyte.

23. The method of claim 18, wherein the analog is a compound having the molecular structure of the analyte.

* * * * *

SEQUENCE LISTING

<160> NUMBER OF SEQ ID NOS: 7

<210> SEQ ID NO 1
<211> LENGTH: 56
<212> TYPE: DNA
<213> ORGANISM: Artificial Sequence
<220> FEATURE:
<223> OTHER INFORMATION: examplary sequence used for illustration

<400> SEQUENCE: 1
gtcagagaga catggtggtg ttgtggttgg tgtgtgttgg ttgtgtgtgg tgttgg          56

<210> SEQ ID NO 2
<211> LENGTH: 28
<212> TYPE: DNA
<213> ORGANISM: Artificial Sequence
<220> FEATURE:
<223> OTHER INFORMATION: examplary sequence used for illustration

<400> SEQUENCE: 2
tttgattatt ctaaatgttg ttaaagag                                        28

<210> SEQ ID NO 3
<211> LENGTH: 28
<212> TYPE: DNA
<213> ORGANISM: Artificial Sequence
<220> FEATURE:
<223> OTHER INFORMATION: examplary sequence used for illustration

<400> SEQUENCE: 3
aaactaataa gatttacaac aatttctc                                        28

<210> SEQ ID NO 4
<211> LENGTH: 9
<212> TYPE: DNA
<213> ORGANISM: Artificial Sequence
<220> FEATURE:
<223> OTHER INFORMATION: examplary sequence used for illustration

<400> SEQUENCE: 4 gagacaugg                                                              9

<210> SEQ ID NO 5
<211> LENGTH: 57
<212> TYPE: DNA
<213> ORGANISM: Artificial Sequence
<220> FEATURE:
<223> OTHER INFORMATION: examplary sequence used for illustration

<400> SEQUENCE: 5
accaacacca cacacaacca acacacacca accacaacac caccatgtct ctctgac         57

<210> SEQ ID NO 6
<211> LENGTH: 28
<212> TYPE: DNA
<213> ORGANISM: Artificial Sequence
<220> FEATURE:
<223> OTHER INFORMATION: examplary sequence used for illustration

<400> SEQUENCE: 6
aaactaataa gatttacaac aatttctc                                        28

<210> SEQ ID NO 7
<211> LENGTH: 51

```
-continued

<212> TYPE: DNA
<213> ORGANISM: Artificial Sequence
<220> FEATURE:
<223> OTHER INFORMATION: examplary sequence used for illustration

<400> SEQUENCE: 7
accaacacca cacacaacca acacacacca accacaacac caccatgtct c         51
```